United States Patent [19]
Kiuregyan et al.

[11] Patent Number: 6,006,587
[45] Date of Patent: Dec. 28, 1999

[54] METHOD AND DEVICE FOR DETERMINING THE KNOCK RATING OF MOTOR FUELS

[75] Inventors: Suren Kiuregovich Kiuregyan, g.Ramenskoe Moscowskaya obl.; Sergei Azatovich Kazarian; Igor Alexandrovich Dovlatov, both of Moscow, all of Russian Federation

[73] Assignee: Aktsionernoe Obschestvo Zakrytogo Tipa Biotekhinvest, Moscow, Russian Federation

[21] Appl. No.: 08/793,632

[22] PCT Filed: Sep. 5, 1994

[86] PCT No.: PCT/RU94/00210

§ 371 Date: Jun. 25, 1997

§ 102(e) Date: Jun. 25, 1997

[87] PCT Pub. No.: WO96/07897

PCT Pub. Date: Mar. 14, 1996

[51] Int. Cl.$^6$ ..................................................... G01N 33/22
[52] U.S. Cl. .......................................... 73/35.02; 73/23.31
[58] Field of Search ................................ 73/23.31, 35.02, 73/35.01, 112, 113, 116, 117.1

[56] References Cited

U.S. PATENT DOCUMENTS

| | | | |
|---|---|---|---|
| 3,010,312 | 11/1961 | Jezl | 73/35.02 |
| 3,318,136 | 5/1967 | Payne et al. | 73/35.02 |
| 3,451,402 | 6/1969 | Howard | 73/35.02 |
| 3,456,492 | 7/1969 | Ludt et al. | 73/35.02 |
| 3,485,598 | 12/1969 | Jones et al. | 73/35.02 |
| 3,561,035 | 2/1971 | Beal | 73/35.02 |
| 3,575,939 | 4/1971 | Beal | 73/35.02 |
| 3,690,851 | 9/1972 | Jones et al. | 73/35.02 |
| 3,738,810 | 6/1973 | Clinton et al. | |
| 3,913,380 | 10/1975 | Jones et al. | 73/35.02 |
| 3,949,595 | 4/1976 | Jones et al. | 73/35.02 |
| 4,010,358 | 3/1977 | Morris | 73/35.02 |
| 4,331,024 | 5/1982 | Childs et al. | 73/35.02 |
| 4,402,212 | 9/1983 | Childs | 73/35.02 |
| 4,708,113 | 11/1987 | Harada et al. | 73/35.02 |

*Primary Examiner*—Richard Chilcot
*Assistant Examiner*—Eric S. McCall
*Attorney, Agent, or Firm*—Kenyon & Kenyon

[57] ABSTRACT

The invention relates to the oil refining and petrochemical industry and concerns, in particular, techniques for determining the knock rating of motor fuels. The proposed method of determining the knock rating of motor fuels involves thermostatic control of a reaction vessel of constant volume, feeding the fuel-air mixture into the vessel, atomization of the mixture under excess pressure and ignition of the mixture. The knock rating is calculated by the knocking intensity which is determined by the value of the signal from a knock sensor installed in the reaction vessel. The proposed apparatus for determining the knock rating of motor fuels comprises a reaction vessel with inlet and outlet valves and a thermostatic controller. A spark plug is installed in the reaction vessel and a knock sensor is arranged opposite the spark plug.

10 Claims, 4 Drawing Sheets

METHOD AND DEVICE FOR DETERMINING THE KNOCK RATING OF MOTOR FUELS

FIELD OF THE INVENTION

The invention relates to area of oil refining and petrochemical industry and concerns in particular techniques of determining of the knock rating of motor fuels.

BACKGROUND ART

There are known an engine method (Fuel for engines. An engine method for determining of octane rating. The USSR State Standard 511-82, ASTM D 2700, DIN 51756) and an analyze method (Fuel for engines. An analyze method for determining of octane rating. The USSR State Standard 8226-82, ASTM D 2699, DIN 51756) for determining of the knock rating of fuels including feeding the fuel into a reaction vessel with variable degree of compression, atomization and ignition of a mixture, determining the knock rating. The method is performed on a one-cylinder engine having variable degree of compression, and the knock rating is expressed by octane rating numerically equal to percentage of isooctane in such a mixture with normal heptane, knock intensity of which in a one-cylinder engine having variable degree of compression in standard conditions of testing is equivalent to knock intensity of the tested fuel.

The methods based on engine tests correctly, in general, characterize fuels, but exhibit significant drawbacks. Those drawbacks include considerable duration of testing and large consumption of tested fuel. So, testing of one sample of fuel using the engine or research methods lasts for 20 minutes and consumes a tested sample of 300 ml. Intense exhaust into atmosphere of harmful products of combustion is one of negative consequences of the large fuel consumption. Because of large consumption of the sample, these methods practically cannot be used for testing of products, obtained on micro-pilot plants.

Besides, it is very difficult to include these methods into a technological scheme for on-stream testing of the products or to use them in a system of automatic control. Furthermore, engines used in the mentioned methods are quite expensive and cumbersome.

The closest on technical essence and achieved result is a method based on initiation of low temperature reaction of gaseous phase oxidation of fuel. The method provides thermostatic control of the reaction vessel of constant volume up to temperatures 250–350° C., feeding of a portion of tested fuel, mixing it with air contained in the vessel at atmospheric pressure, cool flame oxidation of the formed combustible mixture. Temperature in the reaction vessel increases. The knock rating of motor fuel is characterized by temperature gain and time of achieving of maximal temperature. With deterioration of the knock rating of a sample, the temperature is increased, and the time of achieving of maximal temperature is reduced (U.S. Pat. No. 3,738,810, G01L 23/22, 1973).

Methods and devices based on studying of cool flame processes have number of advantages: they are rather inexpensive, application thereof requires insignificant amount of a sample, they could be easily included into a technological system for on-stream testing of products, and they could also be used in a system of automatic control. They possess, however, one quite essential drawback; testing of fuel is performed in conditions rather far from engine operational conditions. Knocking occurs in an engine during combustion of fuel, but in the considered method combustion does not occur at all. Using this method there could be studied phenomena occurring to fuel during preparation for combustion, pre-combustion processes. The distinction between conditions of fuel combustion in an engine and its testing in conditions of cool flame oxidation limits possibilities of the given testing method. The mentioned method gives satisfactory results at testing of homogeneous fuels samples of known composition with insignificant changes, for example, at the output of the technological system. If fuel composition is unknown, the results of testing may be unreliable. Besides, employing of this method, it is practically impossible to estimate efficiency of antiknock additions, since the mechanism of their action is absolutely different, and it is impossible to judge their efficiency using cool flame processes. Therefore, the given method is recommended to use for the control of mixing processes, in which there are not applied antiknock additions, in particular, tetraethyl lead (Clinton R. M., Puzniak T. J. Gulf Research develops continuous-process octane analyzer. Oil and Gas Journal, 1975, 73, No. 16, 77–82).

DISCLOSURE OF THE INVENTION

The invention is based on the problem of providing a method and an apparatus for determining of knock rating of motor fuels in conditions close to operational conditions of an internal-combustion engine.

Technical results, that can be achieved with help of the invention, are improving of reliability of determining of knock rating, widening of area of application thereof, in particular, for estimation of efficiency of antiknock additions, simplifying of determining technique, decreasing of testing duration and consumption of tested fuel, dimensions and cost of equipment and also facilitation of inclusion of the apparatus into flow of the technological system and automatic control system.

This problem is solved by a method of determining a knock rating of a motor fuel fuels, comprising thermostatic control of a reaction vessel of constant volume, feeding the fuel-air mixture into the vessel and atomization of the mixture under excess pressure. The combustible mixture is then ignited causing knocking and the intensity of the knocking is detected based on a signal from a knock sensor installed in the reaction vessel.

The method and device proposed according to the present invention allow the determination of a knock rating of a fuel based on an intensity of knocking of a combustible mixture ignited in the reactor by a spark discharge. Intensity of knocking is a characteristic of the knock rating of a fuel: the higher the intensity of knocking, the lower the knock rating. Date of intensity of knocking is obtained from a knock sensor installed in the reactor.

One of the embodiments of the method of determining the knock rating of motor fuels according to the present invention applies an electric-air system of thermostatic control for the thermostatic control of the reaction vessel.

Another embodiment of the method of determining the knock rating of motor fuels according to the present invention applies an electric-liquid system for the thermostatic control of the reaction vessel. As a cooling liquid there could be used, for example, distilled water or ethylene glycol, depending on a choice at development of the testing procedure, during testing this cooling liquid is in a boiling condition.

Conditions of testing of a fuel in both embodiments are selected depending on knock rating thereof by changing the pressure of air and amount of fuel doze fed into the reaction vessel.

Both for the fuel being tested and for a reference fuel fuel at each air pressure value there is selected a fuel dose ensuring maximum intensity of the knocking. Air pressure is changed until for the tested fuel a knocking intensity accepted as standard for this technique is achieved. Then, and at this value of air pressure the tested fuel is compared with reference fuels. Under action of compressed air the fuel dose is superseded from fuel system, is atomized and mixed with air in a mixing chamber, it is warmed up to a given temperature by an electrical heater and is forced into the reaction vessel, where it is ignited by an electrical spark. Intensity of a knock is evaluated by value of maximal signal from the knock sensor appearing owing to knock combustion of fuel in the reaction vessel and by time of achieving of this maximum from the moment of discharging of the spark.

For estimation of intensity of knocking there is used a knock sensor. We used a magnetostrictive knock sensor. Operation of the knock sensor is based on magnetostrictive effect. Under action of knock waves there is occurring vibrating deformation of a magnetostrictive core, and in a winding of the core there is inducted electrical voltage proportional to knock intensity. This voltage is registered by an oscillograph or other measuring device, and intensity of the knocking is evaluated by value thereof. The magnetostrictive sensor is not a sole device for measuring of knock intensity. For this purpose it is also possible to use, for example, a piezo sensor which under action of knock waves also generates an electrical signal.

Values of temperature of the reaction vessel and fuel-air mixture before forcing into the reaction vessel are selected during development of the procedure and are not changed hereinafter. After combustion of fuel in the reaction vessel the outlet valve is opened and products of combustion are charged out, then the reaction vessel is blown through by clean air and there could be started a new cycle of testing. Controlling of valves, ignition and cycles of testing is performed by a programmer.

The proposed method is realized in an apparatus according to the present invention for determining of knock rating of motor fuels containing a reaction vessel with inlet and outlet valves and having means of thermostatic control. In the reaction vessel there are installed a spark plug and a knock sensor located opposite to the spark plug.

The reaction vessel can be implemented in form of a steel cylinder.

For performing of determining according to the first embodiment there is used an apparatus containing a reaction vessel with electric-air system of thermostatic control equipped by cooling fins, a thermocouple, an inlet and an outlet valve, an electrical spark plug and a knock sensor installed opposite to the spark plug. In order to maintain a required thermal mode in the reaction vessel, there are applied means for control and management.

According to the second embodiment there is used an apparatus containing a reaction vessel in form of a steel cylinder equipped by an inlet and an outlet valves, an electrical spark plug and a knock sensor installed opposite to the spark plug. In order to maintain a required thermal mode of the reaction vessel there is applied a system for electric-liquid thermostatic control consisting of a cooling jacket around the reaction vessel, a condenser of vapors of the cooling liquid, a heater, a measuring glass and a control thermometer.

Distilled water or ethylene glycol could be, for example, applied in the apparatus as a cooling liquid, depending on selection in course of the development of the testing procedure, and during the testing the cooling liquid is in a boiling condition.

Except the system of thermostatic control, the apparatuses according to both embodiments are identical.

A method and an apparatus proposed according to the present invention allow determination of the knock rating of a fuel by intensity of knocking of the combustible mixture ignited in a reactor by a spark discharge. Intensity of knocking is a characteristic of knock rating of the fuel: the higher the intensity of knocking, the lower the knock rating. Data concerning intensity of knocking is received from a knock sensor installed in the reactor.

The advantages specified above and the peculiarities of the present invention will now be described with references to the preferred embodiments of the invention, with reference to the accompanying drawings.

BRIEF DESCRIPTION OF THE DRAWINGS

The method and the apparatus are explained with reference to the following drawings:

FIGS. 3–6 and the Table represent signals from a magnetostrictive knock sensor at combustion of various fuels. The experiments were carried out in a steel cylindrical reactor with internal diameter of 60 mm and length 145 mm. The temperatures were determined with help of a thermocouple installed inside the reactor.

BEST METHOD OF CARRYING OUT THE INVENTION

Figure 1:
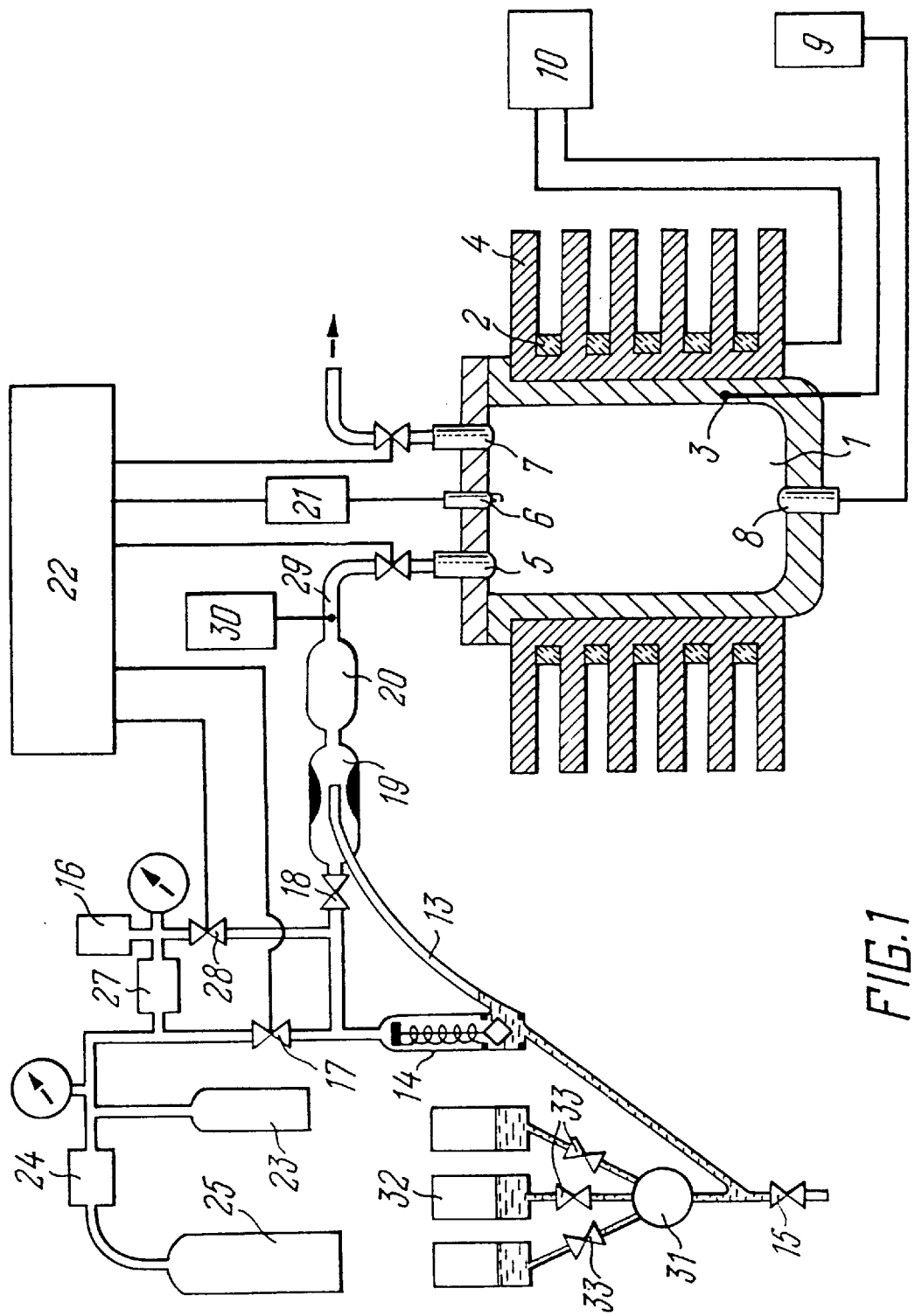
FIG. 1 is a schematic view of an apparatus with an electric-air system of thermostatic control.
Figure 2:
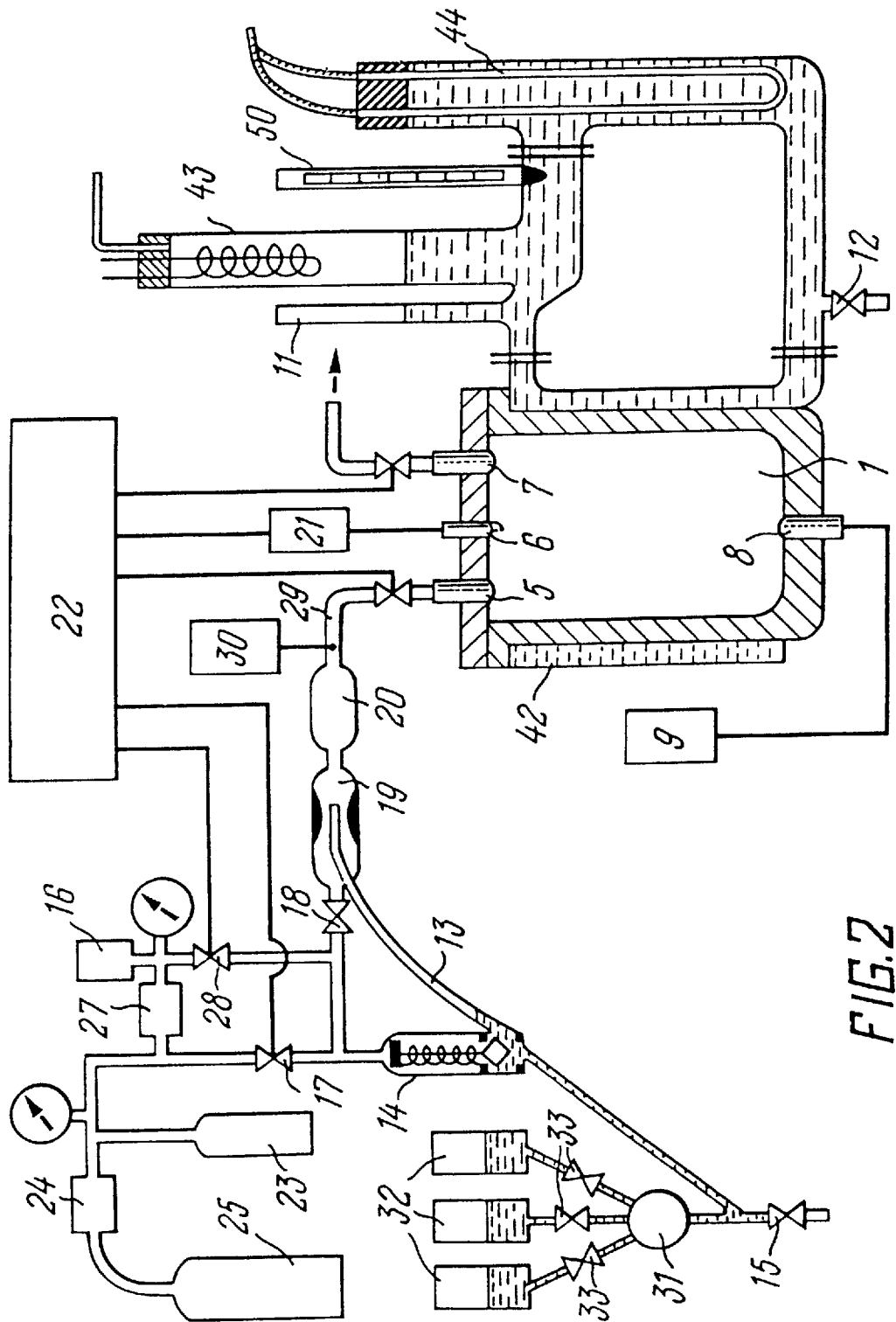
FIG. 2 is a schematic view of an apparatus with an electric-liquid system of thermostatic control.

The apparatus is based on a steel cylindrical reactor 1 with thermostatic control having internal diameter of 40–100 mm, length of 60–200 mm (see FIG. 1 and FIG. 2). Temperature of the reactor is maintained with help of an electric-air system of thermostatic control (FIG. 1) or an electric-liquid system of thermostatic control (FIG. 2).

The electric-air system of thermostatic control (FIG. 1) comprises a heater 2, a thermocouple 3, cooling fins 4 ventilated by a fan and a device 10 for controlling and adjustment of the reactor temperature.

The electric-liquid system of thermostatic control (FIG. 2) consists of a cooling jacket 42, around of the reactor 1, a condenser of vapors of cooling liquid 43, a heater 44, a control thermometer 50 and a measuring glass 11. Other details of both embodiments of the apparatus 20 are identical. On the top cover of the reactor there are installed an inlet and an outlet valves 5 and 7 and a spark plug 6 fed by a block 21. On the bottom cover there is installed a knock sensor 8 connected with a recording apparatus 9.

A necessary amount of tested or reference fuel is fed through the crane-switch 31, is installed by a dosing element 13 and is entered into the mixer 19 for forming of fuel-air mixture which is fed through the heater 20 into the reactor. Temperature of the mixture in range of 500–200° C. is controlled and managed with help of a thermocouple 29 and a regulator 30.

Air is fed into the mixer and reactor through an air line comprising a capacity 25, a reducer 24, a receiver 23, valves 14 and 17, and also a small cylinder 16 for blasting through the reactor. The capacity 25 could be implemented in form of either a compressed air cylinder (150 atm.) or a cylinder pumped up with air by its own compressor. The cylinder 16 has capacity of 0.2–1 l., the receiver 23 is of 2–10 l. capacity, air is fed into the cylinder 16 through the reducer 27 set up for pressure 2–3 atm. and connected with an air line before the valve 17, and air is output through the valve 28 installed after the valve 17.

Tested and reference fuels are placed in tanks 32 and flow by gravity therefrom through the crane-switch 31.

Testing of the fuels is performed as follows. Initially the inlet and outlet valves 5 and 7 are open, valves 14, 17 and 28 are closed. Air and fuel are not fed into the reactor, but dosing element 13 connected by the crane 31 with one of tanks 32 is filled by fuel from this tank. After establishing a desired temperature of the reactor and pressure in the operative receiver 23 the outlet valve 7 is closed and the valve 17 is opened simultaneously. Thus, under pressure of air the valve 14 is passed to the bottom position and the dosing element becomes isolated from the fuel line and connected to the air line. There is performed injection of the fuel-air mixture into the reactor, at the same time the fuel is atomized, evaporates, mixes up with air, is heated up and forms a combustible mixture. At a required interval of time the valves 5 and 17 are closed simultaneously, and the valve 28 is opened, and electrical spark of a spark plug 6 ignites the combustible mixture.

In result of combustion of the mixture, there is formed a knock, the intensity of which depends on knock rating of tested fuel. An electric signal from the knock sensor 8 comes into the recording apparatus 9, where there are recorded parameters thereof: maximal level of the signal formed due to knock combustion of the fuels in the reactor and time of achieving of this maximum from the moment of discharging of the spark. During development of the procedure there should be solved a question what should be taken into consideration at comparison of tested fuel with the standards: either maximal level of the signal, or rate of this maximal level to time of achieving thereof.

After combustion of the mixture the outlet valve 7 is opened, through which there is performed exhaust of combustion products from the reactor, time of opening of the outlet valve is 0.5–2 sec. after sending of voltage onto the spark plug. In 1–3 sec. after opening of the outlet valve 7 the inlet valve 5 is opened and there is performed blasting through of the reactor by clean air from the cylinder 16. Duration of blasting through the reactor is 1–3 sec. The valve 28 is closed. Normally the valve 28 is in a closed position, therefore, there is maintained a constant required pressure in the cylinder 16. The inlet and outlet valves 5 and 7 remain open. On this the cycle is completed.

Because of the pressure in the air line drops up to atmospheric pressure, valve 14 of the dosing element passes into the top position, the dosing element become disconnected from the air line and connected to the fuel line.

A new cycle begins with filling of the dosing element with fuel, thus, due to an open position of valves 5 and 7, there is atmospheric pressure in the dosing element. Duration of a pause between cycles is established by practical consideration during development of the procedure.

Controlling of the valves, ignition and testing cycles is performed by the programmer 22. Process of testing of fuels is basically similar to the standard technique of determining of octane ratings with using of engine testing systems.

Dimensions of the reactor and other units could be finally determined during development of the apparatus design, being guided by the necessity of achievement of optimum testing results.

In a process of development of a procedure there are selected a thermal mode, knocking intensity, at which the tested sample is compared with the standards, time intervals between operations.

Pressure of air for each tested sample, depending on its knock rating, is selected in process of testing, so that knock intensity would not fall outside the limits of values accepted for the technique. Thus, for each value of air pressure there is selected such a dose of fuel, which provides maximal knocking intensity.

The present invention is further illustrated by the following examples.

EXAMPLE 1

Figure 3:
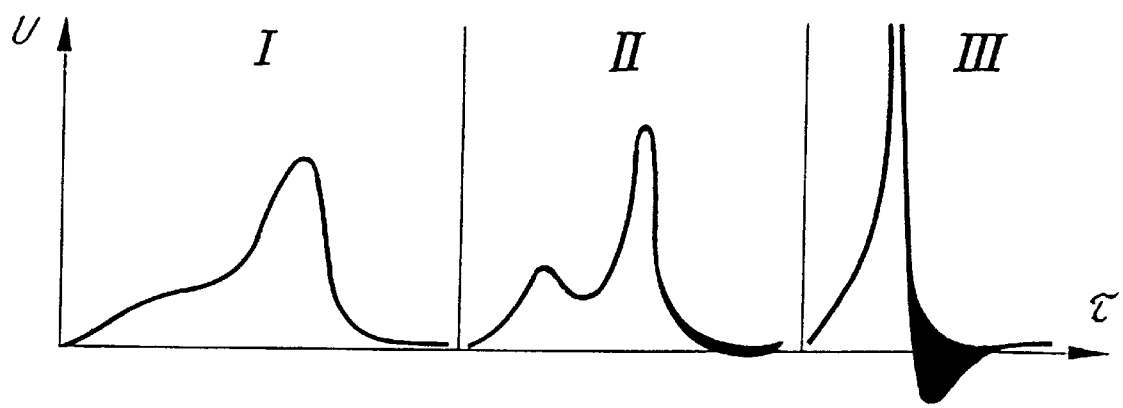
FIG. 3 is diagrams of knock characteristics of normal heptane in testing at a pressure of 3 atm. and at temperatures of 150, 210 and 265° C.

On FIG. 3 there are shown results of testing performed on normal heptane at constant pressure of 3 atm., but at various temperatures: 150, 210 and 265° C. With increasing of temperature, combustion become more severe, and signal from the knock sensor sharply increases.

EXAMPLE 2

Figure 4:
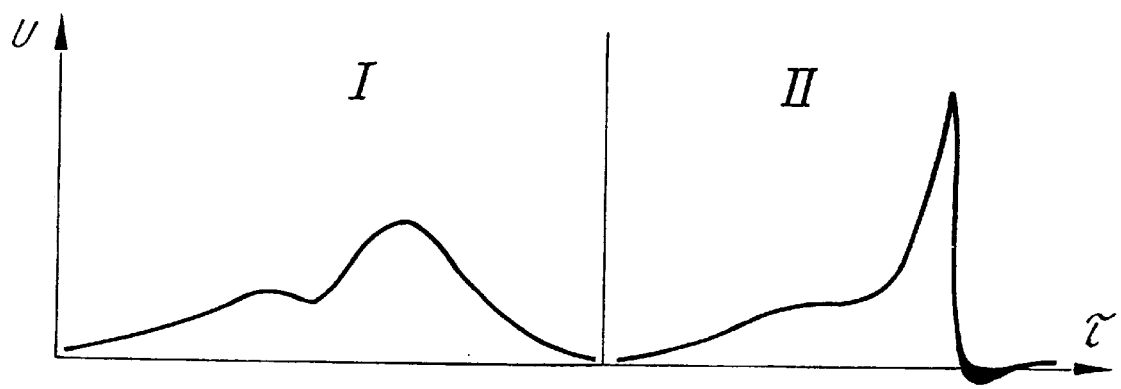
FIG. 4 is diagrams of knock characteristics of isooctane and normal heptane in testing at a pressure of 3 atm. and at a temperature of 210° C.

In order to be convinced, that we observe just a knock, a test in identical conditions was performed on isooctane and normal heptane. It is known, that the isooctane differs from normal heptane by improved knock rating only. On FIG. 4 there are presented records of oscillograph indications, corresponding to the results of testing of isooctane and normal heptane. As it is clear from FIG. 4, the curve—isooctane signal—has a smooth form, while the signal from normal heptane has sharp high peak—obvious affirmation of a knock.

EXAMPLE 3

Figure 5:
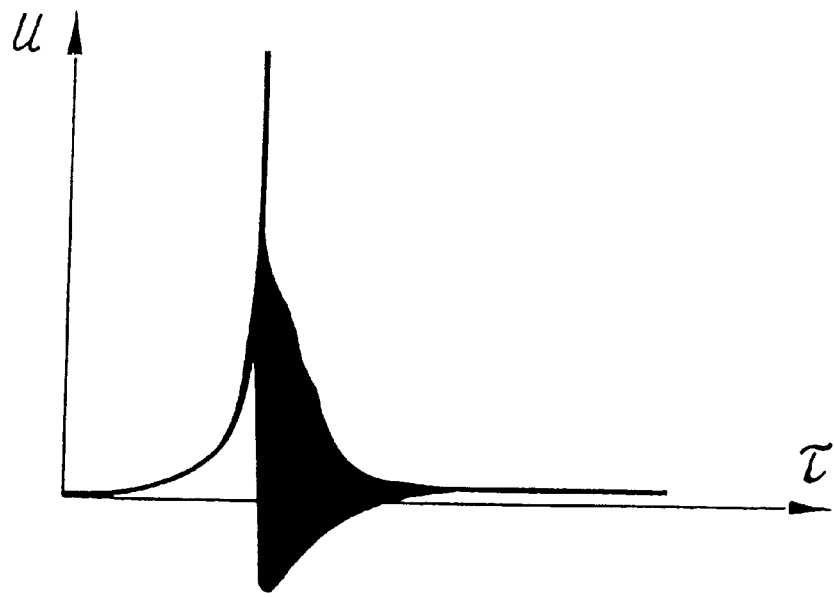
FIG. 5 is a diagram of knock characteristics of isooctane in testing at a pressure of 10 atm. and at a temperature of 305° C.

The method and the apparatus allow to achieve knock effect also at testing of isooctane, however, at more severe conditions (under air pressure of 10 atm. and at temperature 305° C.). The obtained curve is shown on FIG. 5.

EXAMPLE 4

With the purpose of studying of data concerning changing of knock intensity depending on fuel composition, there were performed serial testing of fuels with following content of isooctane and normal heptane (%): 67:33; 75:25; 85:15; 100:0.

TABLE (Test conditions: pressure 3 atm., temperature - 260° C.)

| | | | | |
|---|---|---|---|---|
| Isooctane content in mixture with normal heptane | 67 | 75 | 85 | 100 |
| Knocking intensity (in | 5.8 | 4.8 | 4.4 | 1.3 |

TABLE-continued (Test conditions: pressure 3 atm., temperature - 260° C.)

conditional units - value
H in oscillograph record)

As there is evident from the data presented in the Table, the knock intensity is reduced in accordance with increasing of isooctane content in a tested sample, in other words, method allows to judge with confidence the knock rating of fuel of mixed composition.

EXAMPLE 5

Figure 6:
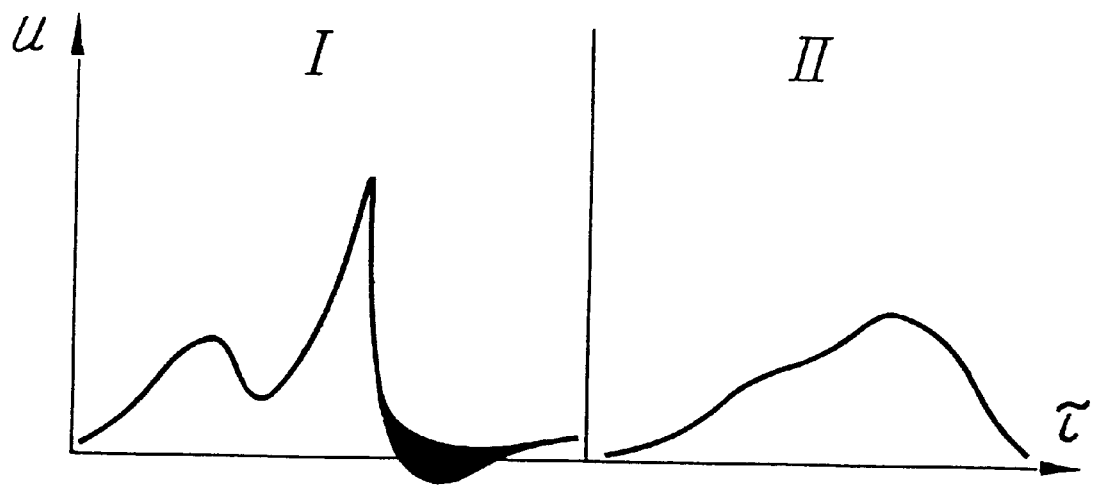
FIG. 6 is a diagram of knock characteristics of pure mixture of isooctane with normal heptane using of antiknock addition (tetraethyl lead).

For achieving the data concerning changing of knocking intensity of fuel in result of application of antiknock additions, there were tested mixtures of 75% of isooctane with 25% of normal heptane in pure state and with additive of tetraethyl lead (TEL) in the ratio of 1 ml. of TEL for 1 l. of fuel. As it is visible on FIG. 6, in contrast to the pure mixture, the knock curve of the fuel with TEL has a cut off peak. Thus, the method allows to estimate knock rating of fuels containing antiknock additions.

Fuel consumption for one measurement depending on pressure of air is 0.05–0.3 ml. Therefore, for fulfillment, for example, of 20 measurements, maximal sample consumption will be not more than 6 ml. Owing to such insignificant samples consumption, all difficulties related to maintenance of testing on micro-pilot plants could be overcome.

When working with a model of the apparatus with manual control and testing results registration, the complete cycle of one measurement comprised no more than 30 sec. Operating an industrial type apparatus having automated control and testing results registration, this time can be reduced up to several seconds.

INDUSTRIAL APPLICABILITY

The proposed method and apparatus can be used in oil refining and petrochemical industry and in analytical practice for research and testing works for determining of knock rating of fuels of various composition, including compositions containing antiknock additions and various components. The proposed apparatus supplied by a programmer, could be easily included in flow of a technological system and in an automatic control system. Other opportunities and advantages of the claimed invention will be apparent to those skilled in the art.

We claim:

1. A method of determining a knock rating of a sample of motor fuel comprising the steps of:

thermostatically controlling a reaction vessel of constant volume;

feeding an atomized mixture of the sample of fuel and air into the reaction vessel at a predetermined excess pressure, wherein the predetermined excess pressure and the temperature of the reaction vessel are controlled to ensure maximal knocking intensity;

igniting the fuel-air mixture in the reaction vessel;

detecting, for each ignition, a knocking intensity of the fuel-air mixture; and determining, for each ignition, the knock rating of the sample of fuel based on a magnitude of the knocking intensity of the fuel-air mixture.

2. A method according to claim 1, wherein an electric-air thermostatic control system is employed in thermostatically controlling the reaction vessel.

3. A method according to claim 1, wherein an electric-liquid thermostatic control system is employed in thermostatically controlling the reaction vessel.

4. A method according to claim 3, wherein one of distilled water and ethylene glycol is employed as a cooling liquid in the electric-liquid thermostatic control system.

5. A method according to claim 1, wherein fuel testing conditions are selected depending on a predicted knock rating of the fuel by varying the predetermined excess pressure and a dose amount of fuel fed into the reaction vessel.

6. An apparatus for determining a knock rating of motor fuel, comprising:

a reaction vessel;

thermostatic control means for maintaining a predetermined temperature within the reaction vessel;

an inlet valve and an outlet valve mounted on the reaction vessel;

a spark plug mounted within the reaction vessel;

a knock sensor mounted within the reaction vessel opposite to the spark plug;

means for determining a knock rating of fuel ignited in the reaction vessel based on a comparison of a magnitude of a signal output from the knock sensor to a value corresponding to a reference fuel.

7. An apparatus according to claim 6, wherein the thermostatic control means comprise an electric heater and an air cooler.

8. An apparatus according to claim 6, wherein the thermostatic control means comprise a cooling jacket, a heater, a condenser for condensing vapor formed by the cooling liquid, a measuring glass and a control thermometer.

9. An apparatus according to claim 6, wherein one of distilled water ethylene glycol is used as a cooling liquid.

10. An apparatus according to claim 6, wherein the reaction vessel is formed as a steel cylinder.

* * * * *